United States Patent [19]

Wistrand et al.

[11] Patent Number: 5,575,905
[45] Date of Patent: Nov. 19, 1996

[54] IODINATION PROCESS

[75] Inventors: Lars-Göran Wistrand, Lund, Sweden; Klaes Golman, Rungsted Kyst, Denmark; Finn Radner, Lund, Sweden

[73] Assignee: Nycomed Imaging AS, Oslo, Norway

[21] Appl. No.: 449,272

[22] Filed: May 24, 1995

[51] Int. Cl.$^6$ ............... C25B 3/06; A61K 49/00; G01N 31/00; C07C 233/00

[52] U.S. Cl. ............... 205/426; 205/431; 205/459; 424/9.45; 424/9.454; 424/9.455; 564/153; 564/155; 564/156; 564/163; 564/170

[58] Field of Search ............... 204/592, 72, 78, 204/81; 424/9.45, 9.455, 9.454; 564/153, 155, 156, 163, 170

[56] References Cited

U.S. PATENT DOCUMENTS

| | | | |
|---|---|---|---|
| 4,348,377 | 9/1982 | Felder et al. | 424/5 |
| 4,495,036 | 1/1985 | So | 205/459 |
| 4,666,570 | 5/1987 | Matsuoka et al. | 204/59 R |
| 5,013,865 | 5/1991 | Cross et al. | 562/456 |
| 5,187,034 | 2/1993 | Otagawa et al. | 429/198 |

FOREIGN PATENT DOCUMENTS

| | | |
|---|---|---|
| 0376858 | 2/1994 | European Pat. Off. . |
| WO92/14695 | 9/1992 | WIPO . |
| WO93/10078 | 5/1993 | WIPO . |
| WO94/14478 | 7/1994 | WIPO . |

OTHER PUBLICATIONS

Miller et al., *Journal of the American Chemical Society*, 92:2821–2825, 1970. (no month).
Miller et al., *Journal of the American Chemical Society*, 98:1515–1519, 1976. (no month).
Torii et al., *Tetrahedron Letters*, 26:1655–1658, 1985. (no month).
Lines et al., *Acta Chem. Scand.,*, B34:47–51, 1980. (no month).
Maysinger et al., *Croat. Chem. Acta*, 49:123–126, 1977. (no month).
Shono et al., *Tetrahedron Letters*, 30(13):1649–1650, 1989. (no month).

*Primary Examiner*—Arun S. Phasge
*Assistant Examiner*—Edna Wong
*Attorney, Agent, or Firm*—Bacon & Thomas

[57] ABSTRACT

The invention provides a process for the preparation of a 2,4,6-triiodinated or 2,4,6,2',4',6'-hexaiodinated 3,5-disubstituted-aniline or 3,3'-disubstituted-5,5'-linked bisaniline, which process comprises electrochemically iodinating a 3,5-disubstituted-aniline or a 3,3'-disubstituted-5,5'-linked bisaniline in an acidic solvent which comprises water and optionally at least one water-miscible organic solvent.

19 Claims, No Drawings

IODINATION PROCESS

FIELD OF THE INVENTION

The present invention relates to a process for the production of monomeric and dimeric triiodophenyl compounds by electrochemical iodination.

BACKGROUND OF THE INVENTION

In diagnostic X-ray imaging, iodine compounds are frequently used as contrast enhancing agents. The compounds used for this purpose for the most part are compounds containing one or two triiodophenyl groups, and thus are often referred to respectively as monomers and dimers.

Examples of commercially available triiodophenyl monomers and dimers include the monomeric compounds acetrizoate, diatrizoate, diodone, iobenzamate, iocetamate, iodamide, iodohippurate, ioglicate, iopamoate, iophendylate, iopronate, iothalamate, oxitalamate, ipodate, metrizoate, iomeprol, iopentol, iopromide, iosimide, ioversol, ioglucol, iogluamide, ioglunide, iogulamide, iosarcol, ioxilan, metrizamide, iopamidol and iohexol, and the dimeric compounds iocarmate, iodipamide, iodoxamate, ioglycamate, ioxaglate, iotroxate, iotasul, iotrolan, iodecimol and iodixanol.

Other monomers and dimers are known from the literature and may be prepared in accordance with the present invention, for example the monomers and dimers referred to in WO-94/14478 (Bracco).

In the conventional processes used for the preparation of these compounds, iodination of the aromatic rings is generally the last or one of the last process steps as in this way utilization of the relatively expensive iodinating agents is optimised.

Thus, for example, in the production of iohexol or iodixanol, the iodination step is conventionally effected using the intermediate 3,5-bis(2,3-dihydroxypropylaminocarbonyl)-aniline.

The iodination reaction, serving to introduce iodines at all of the unsubstituted aromatic ring positions, is conventionally performed using ICl (or its iodide salt analogues such as $KICl_2$ or $NaICl_2$) in an acidic aqueous medium. Examples of such iodination reactions can be found for example in WO-92/14695 (Guerbet) and U.S. Pat. No. 5,013,865 (Mallinckrodt).

These ICl iodination agents are commercially available as corrosive aqueous solutions which have a limited storage life. Furthermore, in the iodination reaction some chlorination may occur as an undesired side-reaction.

Mono-iodination of aromatic species by a procedure known as electrochemical iodination, has been described for example by Shono et al in Tetrahedran Letters 13:1649–1650 (1989). This procedure involves anodic generation from an iodine source of iodide ($I^+$) cations which react to substitute the aromatic ring of a target aromatic compound.

Shono et al (supra) and the other investigators of electrochemical iodination have only suggested its use for introducing a single iodine onto the aromatic ring of the target compound, generally with high paraposition specificity.

It has however now been found that triiodination of the monomeric intermediates and hexaiodination of the dimeric intermediates for the iodinated X-ray contrast agents can be effected in high yield by electrochemical iodination in an acidic solvent mixture which comprises water and optionally at least one water-miscible organic solvent, preferably a polar and/or protic solvent. This route allows the use of cheaper, non-corrosive and highly stable iodine sources (such as iodine and potassium iodide for example) and thus offers significant benefits in the commercial production of iodinated X-ray contrast agents.

SUMMARY OF THE INVENTION

Thus, viewed from one aspect, the present invention provides a process for the preparation of a 2,4,6-triiodinated or 2,4,6,2',4',6'-hexaiodinated 3,5-disubstituted-aniline or 3,3'-disubstituted-5,5'-linked bisaniline, which process comprises electrochemically iodinating a 3,5-disubstituted-aniline or a 3,3'-disubstituted-5,5'-linked bisaniline in an aqueous acidic solvent, eg. a solvent which comprises water and optionally at least one water-miscible organic solvent.

DETAILED DESCRIPTION OF THE INVENTION

In one embodiment, the process of the invention is a process for the preparation of compounds of formula I

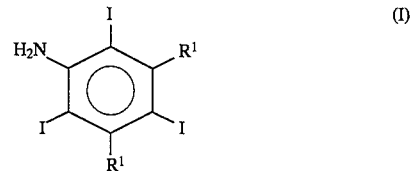

(wherein $R^1$ is as defined below and one $R^1$ group may represent a group of formula II

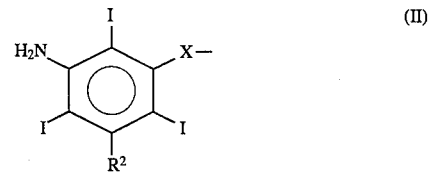

where $R^2$ is as defined for $R^1$ with the exception of the group of formula II and X is a bond or a moiety providing a 1–6 atom chain linking the aromatic rings) by electrochemically iodinating a compound of formula III

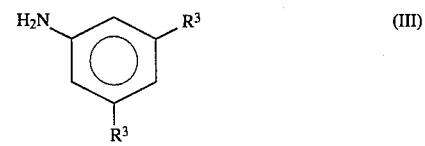

(wherein $R^3$ is as defined below and one $R^3$ group may be a group of formula IV

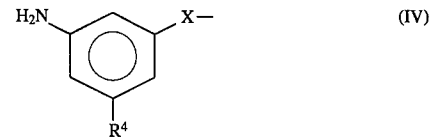

where $R^4$ is as described for $R^3$ with the exception of the group of formula IV).

The substituent groups $R^1$, $R^2$, $R^3$, and $R^4$ may be any of the ionizing or more preferably non-ionizing groups conventionally used to enhance water solubility. Suitable groups include for example straight chain or branched $C_{1-8}$-alkyl groups, preferably $C_{1-5}$ groups, optionally with one or more $CH_2$ or CH moieties replaced by oxygen or nitrogen atoms and optionally substituted by one or more groups selected from oxo, hydroxy, alkoxy, amino, carboxyl, carbonyl derivative, and oxo substituted sulphur and phosphorus atoms. Particular examples include polyhydroxyalkyl, hydroxyalkoxyalkyl and hydroxypolyalkoxyalkyl and such groups attached to the phenyl group via an amide, CO, SO or $SO_2$ linkage such as hydroxyalkylaminocarbonyl, N-alkylhydroxyalkylaminocarbonyl and bis-hydroxyalkylaminocarbonyl groups as well as $COCH_2OH$ and $SO_2CH_2OH$. Preferred among such groups are those containing 1, 2, 3, 4, 5 or 6, especially 1, 2 or 3, hydroxy groups, e.g.

$CONH—CH_2CH_2OH$
$CONH—CH_2\ CHOHCH_2OH$
$CONH—CH(CH_2OH)_2$
$CON(CH_2CH_2OH)_2$ as well as other groups such as $CONH_2$
$CONHCH_3$
$OCOCH_3$
$N(COCH_3)H$
$N(COCH_3)C_{1-3}$-alkyl
$N(COCH_3)$-mono, bis or tris-hydroxy $C_{1-4}$-alkyl
$N(COCH_2OH)$-mono, bis or tris-hydroxy $C_{1-4}$-alkyl
$C(COCH_3)$ (mono, bis or tris-hydroxy $C_{1-4}$-alkyl)$_2$
$N(COCH_2OH)_2$
$CON(CH_2CHOHCH_2OH)$ $(CH_2CH_2OH)$
$CONH-C(CH_2OH)_3$ and
$CONH—CH(CH_2OH)$ $(CHOHCH_2OH)$.

In general, the ring substituent groups will preferably each comprise a polyhydroxy $C_{1-4}$-alkyl group, such as 1,3-dihydroxyprop-2-yl or 2,3-dihydroxyprop-1-yl.

Other such ring substituent groups as are conventional within the field of triiodophenyl X-ray contrast agents may also be used.

Where present, X may be a bond or a 1–7, e.g. 1,2,3 or 4 member atom chain comprising carbon, nitrogen, oxygen or sulphur atoms, e.g. a bond, an O, S, N or CO atom chain, an NCN, OCN, CNC, OCO, NSN, CSN, COC, OCC or CCC atom chain. Examples include: an oxygen atom; a group $NR^6$, CO, $SO_2$ or $CR^6_2$, a group COCO, $CONR^6$, $COCR^6_2$, $SOCR^6_2$, $SO_2NR^6$, $CRhu\ 6_2CR^6_2$, $CR^6_2NR^6$ or $CR^6_2O$ group, a group $NR^6CONR^6$, $OCONR^6$, $CONR^6CO$, $CONR^6CR^6_2$, OCCO, $CR^6_2OCR^6_2$, $OCR^6_2CO$, $CR^6_2CONR^6$, $CR^6_2CR^6_2CR^6_2$, $COCR^6_2CO$, $CR^6_2NR^6CR^6_2$, $CR^6_2SO_2NR^6$, $CR^6_2OCO$ and $NR^6SO_2NR^6$ groups (where $R^6$ is hydrogen or $C_{1-6}$ alkyl or alkoxy optionally substituted by hydroxy, alkoxy, oxa or oxo (e.g. a polyhydroxyalkyl, formyl, acetyl, hydroxy, alkoxy or hydroxyalkyl group, or where attached to a carbon $R^6$ may also be a hydroxy group). When X provides a 4–7 atom linkage, conventional linker groups, such as for example those suggested by WO-93/10078, U.S. Pat. No. 4,348,377 or WO-94/14478 may be used.

In general such linkages will comprise optionally aza or oxa substituted alkylene chains optionally carrying $R^6$ substituents, especially such groups terminating with imine nitrogen or, more preferably, carbonyl carbon atoms, preferably belonging to iminocarbonyl functional units within the chain. Hydroxylated chains, such as are found in iodixanol are particularly preferred.

Examples of such chains are NCCN, NCCCN, CNCCNC, and CNCCN, e.g.
$NR^6COCONR^6$—
$NR^6COCR^6_2CONR^6$—
$NR^6CR^6_2CR^6OHCR^6_2NR^6$—
$CONR^6CR^6_2CONR^6$— and
$N(COR^6)CR^6_2CR^6OHN(COR^6)$—,
e.g. as found in iotrolan, iofratol, ioxaglic acid and iodixanol, or as otherwise indicated in WO-94/14478.

The process of the invention is preferably carried out in a multi-compartment (e.g. 2 or 3 compartment) reaction vessel with porous inter-compartment barriers, for example of glass frit or a permeable membrane material such as Nafion. The anode and the cathode are then preferably disposed in separate compartments and in this way the anodic compartment may be used as the reaction chamber. The aromatic compound which is intended to be iodinated can be added into the reaction vessel as a whole or into the anodic chamber only. Addition can be before, during or after the electrochemical generation of the $I^+$ species.

The anode itself, the working electrode, is preferably of carbon (e.g. graphitic or vitreous carbon), conductive titanium dioxide, platinum or a platinum alloy (e.g. Pt/Ir/Ti). For metal or metal alloy anodes, the anode is conveniently in sheet, plate or gauze form. Platinum gauze and graphitic carbon anodes are preferred.

The nature of the cathode is less important and conventional cathodic materials such as carbon, platinum, palladium, lead, copper and stainless steel or mixtures thereof may be used.

The solvent used is water, optionally together with one or more water-miscible organic co-solvents, preferably a polar and/or protic solvent such as an alkanol (e.g. methanol, ethanol, propanol, iso-propanol or n-butanol), an ether (e.g. a cyclic ether such as tetrahydrofuran), a ketone (such as acetone), a carboxylic acid (such as acetic or trifluoroacetic acid), dimethylformamide or dimethylsulphoxide, or acetonitrile. Acetonitrile or an alkanol such as methanol is generally preferred. Aromatic organic solvents such as toluene should of course not generally be used.

The water to organic co-solvent ratio is preferably 1:3 to 3:1 by weight.

The acidic nature of the solvent system may be achieved by selection of an acidic organic co-solvent such as acetic acid or trifluoroacetic acid or may be by virtue of the inclusion of a strong organic or inorganic acid such as sulphuric or fluroboric acid.

The pH of the solvent system is preferably below 7, particularly 0 to 3, especially 1 to 2.

For the electrochemical generation of $I^+$ to be effective, it is preferred that the solvent system should include an electrolyte species so as to enhance solvent conductivity. The concentration of electrolyte used should be sufficient to give adequate conductivity, for example 1–100% by weight relative to the non-ionic solvents, especially 1–10%. The electrolyte should not of course provide a competing species in the anode compartment and in general fluoroborates, sulphates and perchlorates are preferred, for example lithium perchlorate, tetraethylammonium perchlorate, tetrabutylammonium fluoroborate, tetra-n-propylammoniumfluoroborate, $NaBF_4$, $NaBF_4$, $(CH_3)_4NBF_4$, $Na_2SO_4$ and $(Bu)_4NBF_4$, especially lithium perchlorate, $NaBF_4$, $(CH_3)_4NBF_4$ or $(Bu)_4NBF_4$.

The iodine source used in the process of the present invention may be introduced into the reaction mixture either as a whole or simply into the anodic compartment of the compartmented reaction vessel. For this purpose, iodine or an iodide (such as NaI, KI, HI or an alkylammoniumiodide) may be used. Iodine, KI and NaI are preferred.

The iodine source will preferably be used at a concentration sufficient to provide 100–150% of iodine atoms relative to the unsubstituted ringsites on the target aromatic species. In general, the target compounds will be used at concentrations of from about 0.1 to 1M, and preferred iodine concentrations are thus 0.15 to 2.25M.

In the reaction, a constant voltage is applied across the cathode and anode to generate the $I^+$ species. This voltage is preferably 1–50 V, especially 5–30 V.

During the process of the invention, the reaction mixture is preferably cooled, for example by emersion of the reaction vessel in a water bath or by provision of the reaction vessel with a water jacket so as to maintain the solvent temperature below 25° C.

Following the process of the invention, the iodinated product may be isolated by removal of the organic solvent followed by filtration or chromatography.

The process of the invention is illustrated further by the following non-limiting examples:

EXAMPLE 1

Procedure A for the Electrochemical Iodination

In a water-jacketed cell containing a platinum anode (4×5 cm), a magnetic stirring bar, a cathode compartment separated by a glass frit and a stainless steel cathode (5 cm$^2$) was placed 80 ml of a 0.15M NaBF$_4$ solution in methanol/water (1/1). Iodine (0.76 g, 3.0 mmol) was dissolved in the anolyte and, after adjustment of the pH to 1.5 with aqueous HBF$_4$, a constant current of 200 mA was passed through the solution while the temperature was kept at 20° C. After passage of 3 F/mol I$_2$, the anolyte solution was used for iodination.

EXAMPLE 2

3.5-Bis(2,3-dihydroxypropylaminocarbonyl)-2,4,6-triiodo-aniline

Procedure B for the Electrochemical Iodination (Substrate Present)

In a water-jacketed cell containing a platinum anode (4×5 cm), a magnetic stirring bar, a cathode compartment separated by a glass frit and a stainless steel cathode (5 cm$^2$) was placed 80 ml of a 0.15M NaBF4 solution in methanol/water (1/1). Iodine (0.76 g 0.3mmol) and 3,5-bis(2,3-dihydroxypropylaminocarbonyl)aniline (0.33 g, 1 mmol) was dissolved in the anolyte and, after adjustment of the pH to 1.5 with aqueous HBF$_4$, a constant current of 200 mA was passed through the solution while the temperature was kept at 20° C. After passage of 3 F/mol I$_2$, the anolyte was stirred at 60° C. for 24 h. Analysis by HPLC indicated a quantitative conversion of the substrate into 3,5-bis(2,3-dihydroxypropylaminocarbonyl)-2,4,6-triodoaniline.

EXAMPLE 3:
3,5-Bis(2,3-dihydroxypropylaminocarbonyl)-2,4,6-triodoaniline

To the solution obtained according to Procedure A (Example 1) was added 3,5-bis(2,3-dihydroxypropylaminocarbonyl)-aniline (0.33 g, 1 mmol) dissolved in water (40 ml). After adjustment of the pH to 1.1 with aqueous HBF$_4$, the solution was heated to 80° C. HPLC analysis after 2.5 hours indicated 99.8% conversion to the triiodinated product. Purification by preparative HPLC gave the title product as a white crystalline material (72% isolated yield).

EXAMPLE 4: 3-Hydroxymethyl-5(2,3-dihydroxypropylaminocarbonyl)-2,4,6-triodoaniline To a iodination solution prepared according to Procedure A (Example 1) from 9.9 g of I$_2$ in 400 ml solvent was added 3-hydroxymethyl-5-(2,3-dihydroxypropylaminocarbonyl)-aniline (5 g, 20.8 mmol) dissolved in water (100 ml). The solution was stirred at 60° C. for 8 h. After adjustment of the pH to 5 with aqueous NaOH, methanol was removed by evaporation and the residue was lyophilized. The solid crude product was then redissolved in CH$_2$Cl$_2$/MeOH (7:3, v/v) and filtered through a pad of silica gel. Evaporation gave 10 g (78%) of the title product as a white solid.

$^1$H NMR(300 MHz, CD$_3$OD): 5.21(s, 2H), 3.90–3.98(m, 1H) , 3.22–3.77(m, 4H), 2.14(s, 2H).

EXAMPLE 5

3,5-Bis(2,3-dihydroxypropylaminocarbonyl)-2,4,6-triodoaniline

Procedure C for Electrochemical Iodination (Starting from KI)

In a water-jacketed cell containing a platinum anode (4×5 cm), a magnetic stirring bar, a cathode compartment separated by a glass frit and a stainless steel cathode (5 cm$^2$) was placed 40 ml of a 0.25M NaPF$_6$ solution in methanol/water(1/1) containing KI (0.498 g, 3 mmol). After adjustment of the pH to ca 1.6 using HPF$_6$, a constant current of 200 mA was passed through the solution until 6 F/mol I$^-$ had been consumed. A solution of 3,5-bis (2,3-dihydroxypropylaminocarbonyl)-aniline (0.164 g, 0.5 mmol) in water (20 ml) was added and the mixture was stirred at 40° C. for 96 h. Analysis by HPLC indicated a 65% conversion of the starting material into 3,5-bis(2,3-dihydroxypropylaminocarbonyl)2,4,6-triiodoaniline.

EXAMPLE 6

3-(2,3-Dihydroxypropylaminocarbonyl)-2,4,6-triiodo-5-(3'-amino-2',4',6'-triiodo-5'(2,3-dihydroxypropylaminocarbonyl)-benzoylamino)-aniline To an iodination solution prepared according to Procedure A (Example 1) from I$_2$ (0.99 g,3.9 mmol) in a mixture of methanol (30 ml) and water (10 ml) containing NaBF$_4$ (0.2M) was added 3-(2,3-dihydroxypropyl-aminocarbonyl)-5-(3'-amino-5'-(2,3-dihydroxypropylaminocarbonyl)-benzoylamino)-aniline (0.66 g, 1.04 mmol) dissolved in a mixture of methanol and water (5 ml, 3:1). The solution was stirred for at 40° C. for 48 hours. After addition of aqueous NaHSO$_3$ and neutralisation with aqueous NaHCO$_3$, the solvents were evaporated. HPLC analysis of the residue indicated a greater than 90% conversion to the desired product.

We claim:

1. A process for the preparation of a 2,4,6-triiodinated-3, 5-disubstituted-aniline or a 2,4,6,2',4',6'-hexaiodinated-3,3'-disubstituted-5,5'-linked bisaniline, which process comprises electrochemically iodinating a 3,5-disubstituted-aniline or a 3,3'-disubstituted-5,-5'-linked bisaniline in an aqueous acidic solvent.

2. A process as claimed in claim 1 wherein said acidic solvent comprises at least one water-miscible organic solvent.

3. A process as claimed in claim 2 wherein said organic solvent is a polar or protic solvent.

4. A process as claimed in claim 3 wherein said organic solvent is selected from the group consisting of alkanols, ethers, ketones, carboxylic acids, dimethylformamide, dimethylsulphoxide and acetonitrile.

5. A process as claimed in claim 1 for the preparation of compounds of formula I

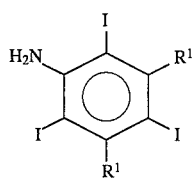

wherein each $R^1$ independently represents a hydrophilic group or one $R^1$ group represents a hydrophilic group and the other $R^1$ group may represent a group of formula II

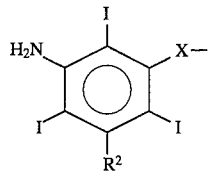

$R^2$ is as defined for $R^1$ with the exception of the group of formula II and X is a bond or a moiety providing a 1–7 atom chain linking the aromatic rings, which process comprises electrochemically iodinating a compound of formula III

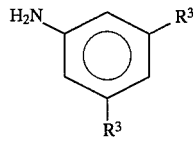

wherein each $R^3$ independently represents a hydrophilic group or one $R^3$ group represents a hydrophilic group and the other $R^3$ group represents a group of formula IV

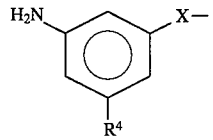

where $R^4$ is as described for $R^3$ with the exception of the group of formula IV.

6. A process as claimed in claim 5 wherein in formula I, II, III and IV hydrophilic $R^1$, $R^2$, $R^3$ or $R^4$ groups are straight chain or branched $C_{1-8}$-alkyl groups with one or more $CH_2$ or CH moieties replaced by oxygen or nitrogen atoms or substituted by one or more groups selected from oxo, hydroxy, alkoxy, amino, carboxyl, carboxyl derivative, and oxo substituted sulphur and phosphorus atoms.

7. A process as claimed in claim 5 wherein in formula I, II, III and IV hydrophilic $R^1$, $R^2$, $R^3$ or $R^4$ groups are polyhydroxyalkyl, hydroxyalkoxyalkyl and hydroxypolyalkoxyalkyl optionally attached to the phenyl group via an amide, CO, SO or $SO_2$ linkage.

8. A process as claimed in claim 5 wherein in formula I, II, III and IV hydrophilic $R^1$, $R^2$, $R^3$ or $R^4$ groups are hydroxyalkylaminocarbonyl, N-alkylhydroxyalkylaminocarbonyl, bis-hydroxyalkylaminocarbonyl, $COCH_2OH$ or $SO_2CH_2OH$ groups.

9. A process as claimed in claim 5 wherein in formula I, II, III and IV hydrophilic $R^1$, $R^2$, $R^3$ or $R^4$ groups are $CONH—CH_2CH_2OH$,
$CONH—CH_2CHOHCH_2OH$,
$CONH—CH(CH_2OH)_2$,
$CON(CH_2CH_2OH)_2$,
$CONH_2$,
$CONHCH_3$,
$OCOCH_3$,
$N(COCH_3)H$,
$N(COCH_3)C_{1-3}$-alkyl,
$N(COCH_3)$-mono, bis or tris-hydroxy $C_{1-4}$-alkyl,
$N(COCH_2OH)$-mono, bis or tris-hydroxy $C_{1-4}$-alkyl,
$C(COCH_3)$ (mono, bis or tris-hydroxy $C_{1-4}$-alkyl)$_2$,
$N(COCH_2OH)_2$,
$CON(CH_2CHOHCH_2OH)$ $(CH_2CH_2OH)$,
$CONH-C(CH_2OH)_3$ and
$CONH—CH(CH_2OH)$ $(CHOHCH_2OH)$ groups.

10. A process as claimed in claim 5 wherein in the compound of formula III each aminophenyl ring is substituted by at least one polyhydroxy $C_{1-4}$-alkyl group.

11. A process as claimed in claim 5 wherein in the compound of formula III X is a bond, an oxygen atom, or a group selected from $Nr^6$, CO, $SO_2$, $CR^6_2$, COCO, $CONR^6$, $COCR_2^6$, $SOCR_2^6$, $SO_2NR^6$, $CR^6_2CR^6_2$, $CR^6_2NR^6$, $CR^6_2O$, $NR^6CONR^6$, $OCONR^6$, $CONR^6CO$, $CONR^6CR^6_2$, OCCO, $CR^6_2OCR^6_2$, $OCR^6_2CO$, $CR^6_2CONR^6$, $CR^6_2CR^6_2CR^6_2$, $COCR^6_2CO$, $CR^6_2NR^6CR^6_2$, $CR^6_2SO_2NR^6$, $CR^6_2OCO$ and $NR^6SO_2NR^6$, where $R^6$ is hydrogen or $C_{1-6}$ alkyl or alkoxy optionally substituted by hydroxy, alkoxy, oxa or oxo group.

12. A process as claimed in claim 5 wherein said compound of formula III is 3,5-tris (2,3-dihydroxypropylaminocarbonyl)aniline.

13. A process as claimed in claim 5 wherein said compound of formula III is 3-hydroxyethyl-5-(2,3-dihydroxypropylaminocarbonyl)aniline.

14. A process as claimed in claim 5 wherein said compound of formula III is 3-(2,3-dihydroxypropylaminocarbonyl)5-(3'-amino-5'-(2,3-dihydroxypropylaminocarbonyl)-benzoylamino)aniline.

15. A process as claimed in claim 1 wherein said electroiodination is effected in a multi-compartment reaction vessel with porous inter-compartment barriers, with an anode and a cathode disposed in separate compartments in said vessel.

16. A process as claimed in claim 1 wherein said electroiodination is effected using an anode of carbon, titanium dioxide, platinum or a platinum alloy.

17. A process as claimed in claim 1 wherein said acidic solvent contains a fluoroborate, sulphate or perchlorate electrolyte.

18. A process as claimed in claim 1 further comprising the step of isolating the iodinated product.

19. A process as claimed in claim 1 wherein the aqueous acidic solvent has a pH of 0 to 3.

* * * * *